(12) United States Patent
Locke et al.

(10) Patent No.: US 11,045,593 B2
(45) Date of Patent: Jun. 29, 2021

(54) REDUCED-PRESSURE SYSTEMS AND METHODS EMPLOYING A LEAK-DETECTION MEMBER

(71) Applicant: KCI Licensing, Inc., San Antonio, TX (US)

(72) Inventors: Christopher Brian Locke, Bournemouth (GB); Timothy Mark Robinson, Shillingstone (GB); Aidan Marcus Tout, Alderbury (GB); Justin Alexander Long, Wimborne (GB)

(73) Assignee: KCI Licensing, Inc., San Antonio, TX (US)

( * ) Notice: Subject to any disclaimer, the term of this patent is extended or adjusted under 35 U.S.C. 154(b) by 154 days.

(21) Appl. No.: 15/449,551

(22) Filed: Mar. 3, 2017

(65) Prior Publication Data
US 2017/0224890 A1  Aug. 10, 2017

Related U.S. Application Data

(63) Continuation of application No. 13/571,860, filed on Aug. 10, 2012, now Pat. No. 9,622,914.
(Continued)

(51) Int. Cl.
*A61M 1/00* (2006.01)
*A61F 13/00* (2006.01)
(Continued)

(52) U.S. Cl.
CPC ..... *A61M 1/0088* (2013.01); *A61F 13/00068* (2013.01); *A61F 13/0206* (2013.01);
(Continued)

(58) Field of Classification Search
CPC combination set(s) only.
See application file for complete search history.

(56) References Cited

U.S. PATENT DOCUMENTS 1,355,846 A  10/1920 Rannells
2,547,758 A   4/1951 Keeling
(Continued)

FOREIGN PATENT DOCUMENTS

AU  550575 B2  3/1986
AU  745271 B2  3/2002
(Continued)

OTHER PUBLICATIONS

"Wikipedia for Universal Indicator" for litmus paper using color change as Wikipedia citing references published 1933, 1934, 1937, 2006, 2007 (https://en.wikipedia.org/wiki/Universal_indicator); (Year: 2020).*

(Continued)

*Primary Examiner* — Guy K Townsend (57) ABSTRACT

Systems, methods, and apparatus are provided for detecting leaks in systems for treating a patient with reduced pressure. In one instance, a system includes a distribution manifold for disposing proximate to the tissue site and a sealing member for disposing over the distribution manifold and at least a portion of intact epidermis of the patient. The sealing member has at least a portion that is substantially transparent. The system further includes a reduced-pressure source associated with the distribution manifold for providing reduced pressure to the distribution manifold and a leak-detection member sized and configured to substantially surround the distribution manifold. The leak-detection member includes a detection material that develops a color contrast when a portion is exposed to air and a portion is not exposed to air. The leak detection member works with even low flow systems. Other systems, methods, and apparatus are presented.

23 Claims, 5 Drawing Sheets

Related U.S. Application Data (60) Provisional application No. 61/534,566, filed on Sep. 14, 2011.

(51) Int. Cl.
 *A61H 7/00* (2006.01)
 *A61F 13/02* (2006.01)

(52) U.S. Cl.
 CPC ......... *A61F 13/0216* (2013.01); *A61H 7/001* (2013.01); *A61M 1/009* (2014.02); *A61F 2013/0094* (2013.01); *A61F 2013/0097* (2013.01); *A61F 2013/00174* (2013.01); *A61F 2013/00536* (2013.01); *A61F 2013/00795* (2013.01); *A61F 2013/00846* (2013.01); *A61F 2013/00885* (2013.01); *A61F 2013/00948* (2013.01); *A61M 2205/0216* (2013.01); *A61M 2205/15* (2013.01); *A61M 2205/3306* (2013.01); *A61M 2205/6081* (2013.01); *A61M 2207/00* (2013.01)

(56) References Cited

U.S. PATENT DOCUMENTS

| | | | |
|---|---|---|---|
| 2,632,443 | A | 3/1953 | Lesher |
| 2,682,873 | A | 7/1954 | Evans et al. |
| 2,910,763 | A | 11/1959 | Lauterbach |
| 2,969,057 | A | 1/1961 | Simmons |
| 3,066,672 | A | 12/1962 | Crosby, Jr. et al. |
| 3,367,332 | A | 2/1968 | Groves |
| 3,520,300 | A | 7/1970 | Flower, Jr. |
| 3,568,675 | A | 3/1971 | Harvey |
| 3,648,692 | A | 3/1972 | Wheeler |
| 3,682,180 | A | 8/1972 | McFarlane |
| 3,826,254 | A | 7/1974 | Mellor |
| 3,902,484 | A * | 9/1975 | Winters ............ A61B 46/00 128/849 |
| 4,080,970 | A | 3/1978 | Miller |
| 4,096,853 | A | 6/1978 | Weigand |
| 4,139,004 | A | 2/1979 | Gonzalez, Jr. |
| 4,165,748 | A | 8/1979 | Johnson |
| 4,184,510 | A | 1/1980 | Murry et al. |
| 4,233,969 | A | 11/1980 | Lock et al. |
| 4,245,630 | A | 1/1981 | Lloyd et al. |
| 4,256,109 | A | 3/1981 | Nichols |
| 4,261,363 | A | 4/1981 | Russo |
| 4,275,721 | A | 6/1981 | Olson |
| 4,284,079 | A | 8/1981 | Adair |
| 4,297,995 | A | 11/1981 | Golub |
| 4,333,468 | A | 6/1982 | Geist |
| 4,373,519 | A | 2/1983 | Errede et al. |
| 4,382,441 | A | 5/1983 | Svedman |
| 4,392,853 | A | 7/1983 | Muto |
| 4,392,858 | A | 7/1983 | George et al. |
| 4,419,097 | A | 12/1983 | Rowland |
| 4,465,485 | A | 8/1984 | Kashmer et al. |
| 4,475,909 | A | 10/1984 | Eisenberg |
| 4,480,638 | A | 11/1984 | Schmid |
| 4,525,166 | A | 6/1985 | Leclerc |
| 4,525,374 | A | 6/1985 | Vaillancourt |
| 4,540,412 | A | 9/1985 | Van Overloop |
| 4,543,100 | A | 9/1985 | Brodsky |
| 4,548,202 | A | 10/1985 | Duncan |
| 4,551,139 | A | 11/1985 | Plaas et al. |
| 4,569,348 | A | 2/1986 | Hasslinger |
| 4,605,399 | A | 8/1986 | Weston et al. |
| 4,608,041 | A | 8/1986 | Nielsen |
| 4,640,688 | A | 2/1987 | Hauser |
| 4,655,754 | A | 4/1987 | Richmond et al. |
| 4,664,662 | A | 5/1987 | Webster |
| 4,710,165 | A | 12/1987 | McNeil et al. |
| 4,733,659 | A | 3/1988 | Edenbaum et al. |
| 4,743,232 | A | 5/1988 | Kruger |
| 4,758,220 | A | 7/1988 | Sundblom et al. |
| 4,787,888 | A | 11/1988 | Fox |
| 4,822,743 | A * | 4/1989 | Wegrzyn ............ G01N 21/91 116/201 |
| 4,826,494 | A | 5/1989 | Richmond et al. |
| 4,838,883 | A | 6/1989 | Matsuura |
| 4,840,187 | A | 6/1989 | Brazier |
| 4,863,449 | A | 9/1989 | Therriault et al. |
| 4,869,271 | A * | 9/1989 | Idris ............ A61B 46/00 128/853 |
| 4,872,450 | A | 10/1989 | Austad |
| 4,878,901 | A | 11/1989 | Sachse |
| 4,897,081 | A | 1/1990 | Poirier et al. |
| 4,903,710 | A * | 2/1990 | Jessamine ............ A61B 46/30 128/849 |
| 4,906,233 | A | 3/1990 | Moriuchi et al. |
| 4,906,240 | A | 3/1990 | Reed et al. |
| 4,919,654 | A | 4/1990 | Kalt |
| 4,941,882 | A | 7/1990 | Ward et al. |
| 4,953,565 | A | 9/1990 | Tachibana et al. |
| 4,969,880 | A | 11/1990 | Zamierowski |
| 4,985,019 | A | 1/1991 | Michelson |
| 5,037,397 | A | 8/1991 | Kalt et al. |
| 5,042,981 | A * | 8/1991 | Gross ............ A61B 18/16 606/32 |
| 5,086,170 | A | 2/1992 | Luheshi et al. |
| 5,092,858 | A | 3/1992 | Benson et al. |
| 5,100,396 | A | 3/1992 | Zamierowski |
| 5,134,994 | A | 8/1992 | Say |
| 5,149,331 | A | 9/1992 | Ferdman et al. |
| 5,154,712 | A * | 10/1992 | Herweck ............ A61M 1/0013 604/321 |
| 5,167,613 | A | 12/1992 | Karami et al. |
| 5,176,663 | A | 1/1993 | Svedman et al. |
| 5,183,763 | A * | 2/1993 | Mallow ............ G01N 33/004 436/106 |
| 5,215,522 | A | 6/1993 | Page et al. |
| 5,218,212 | A * | 6/1993 | Sato ............ G01N 21/783 250/226 |
| 5,232,453 | A | 8/1993 | Plass et al. |
| 5,261,893 | A | 11/1993 | Zamierowski |
| 5,278,100 | A | 1/1994 | Doan et al. |
| 5,279,550 | A | 1/1994 | Habib et al. |
| 5,298,015 | A | 3/1994 | Komatsuzaki |
| 5,322,797 | A * | 6/1994 | Mallow ............ G01N 33/004 436/106 |
| 5,342,376 | A | 8/1994 | Ruff |
| 5,344,415 | A | 9/1994 | DeBusk et al. |
| 5,358,494 | A | 10/1994 | Svedman |
| 5,383,476 | A * | 1/1995 | Peimer ............ A61B 46/00 128/849 |
| 5,386,835 | A * | 2/1995 | Elphick ............ A61F 15/004 128/846 |
| 5,437,622 | A | 8/1995 | Carlon |
| 5,437,651 | A | 8/1995 | Todd et al. |
| 5,527,293 | A | 6/1996 | Zamierowski |
| 5,549,584 | A | 8/1996 | Gross |
| 5,556,375 | A | 9/1996 | Ewall |
| 5,607,388 | A | 3/1997 | Ewall |
| 5,636,643 | A | 6/1997 | Argenta et al. |
| 5,645,081 | A | 7/1997 | Argenta et al. |
| 5,704,905 | A * | 1/1998 | Jensen ............ A61F 13/0259 602/42 |
| 5,753,285 | A * | 5/1998 | Horan ............ C12Q 1/04 426/383 |
| 5,816,252 | A * | 10/1998 | Faries, Jr. ............ A61F 7/0241 128/849 |
| 5,979,226 | A * | 11/1999 | Cavestri ............ C10M 171/007 252/301.16 |
| 6,070,454 | A * | 6/2000 | Cavestri ............ G01M 3/20 250/302 |
| 6,070,455 | A * | 6/2000 | Cavestri ............ G01M 3/20 73/40.7 |
| 6,071,267 | A | 6/2000 | Zamierowski |
| 6,101,867 | A * | 8/2000 | Cavestri ............ C10M 171/007 73/40.7 |
| 6,135,116 | A | 10/2000 | Vogel et al. |
| 6,241,747 | B1 | 6/2001 | Ruff |
| 6,287,316 | B1 | 9/2001 | Agarwal et al. |

(56) References Cited

U.S. PATENT DOCUMENTS

| | | | |
|---|---|---|---|
| 6,345,623 B1 | 2/2002 | Heaton et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,814,079 B2 | 11/2004 | Heaton et al. | |
| 7,014,816 B2* | 3/2006 | Miller | G01N 31/22 422/87 |
| 7,709,694 B2* | 5/2010 | Batich | A61L 15/46 604/360 |
| 7,846,141 B2 | 12/2010 | Weston | |
| 7,858,679 B2* | 12/2010 | Messersmith | C08G 65/3322 524/17 |
| 7,931,630 B2 | 4/2011 | Nishtala et al. | |
| 7,943,380 B2* | 5/2011 | Westman | C09B 67/0083 436/4 |
| 7,994,383 B2* | 8/2011 | Zocher | A61F 15/008 602/58 |
| 8,061,360 B2* | 11/2011 | Locke | A61M 5/1415 128/898 |
| 8,062,273 B2 | 11/2011 | Weston | |
| 8,157,775 B2* | 4/2012 | Bobroff | A61M 1/0003 604/319 |
| 8,211,073 B2* | 7/2012 | Dove | A61F 5/445 604/342 |
| 8,216,198 B2 | 7/2012 | Heagle et al. | |
| 8,251,979 B2 | 8/2012 | Malhi | |
| 8,257,327 B2 | 9/2012 | Blott et al. | |
| 8,343,437 B2* | 1/2013 | Patel | G01K 3/04 422/424 |
| 8,398,614 B2 | 3/2013 | Blott et al. | |
| 8,449,509 B2 | 5/2013 | Weston | |
| 8,500,718 B2* | 8/2013 | Locke | A61M 1/0031 604/543 |
| 8,529,548 B2 | 9/2013 | Blott et al. | |
| 8,535,296 B2 | 9/2013 | Blott et al. | |
| 8,551,060 B2 | 10/2013 | Schuessler et al. | |
| 8,568,386 B2 | 10/2013 | Malhi | |
| 8,679,081 B2 | 3/2014 | Heagle et al. | |
| 8,707,766 B2* | 4/2014 | Harris | G01N 31/225 73/49.3 |
| 8,834,451 B2 | 9/2014 | Blott et al. | |
| 8,926,592 B2 | 1/2015 | Blott et al. | |
| 9,017,302 B2 | 4/2015 | Vitaris et al. | |
| 9,198,801 B2 | 12/2015 | Weston | |
| 9,211,365 B2 | 12/2015 | Weston | |
| 9,289,542 B2 | 3/2016 | Blott et al. | |
| 2002/0044891 A1* | 4/2002 | Miller | G01N 31/22 422/421 |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2004/0030304 A1* | 2/2004 | Hunt | A61L 15/22 604/317 |
| 2004/0200480 A1* | 10/2004 | Faries, Jr. | A61B 46/10 128/849 |
| 2004/0200483 A1* | 10/2004 | Faries, Jr. | A61F 7/0085 128/894 |
| 2004/0208780 A1* | 10/2004 | Faries, Jr. | A61B 46/10 422/3 |
| 2004/0258562 A1* | 12/2004 | Mills | G01J 1/50 422/400 |
| 2005/0112772 A1* | 5/2005 | Farone | G01N 21/78 436/151 |
| 2006/0194324 A1* | 8/2006 | Faries, Jr. | A61B 50/13 436/1 |
| 2007/0078366 A1* | 4/2007 | Haggstrom | A61F 13/00063 602/53 |
| 2007/0089753 A1* | 4/2007 | Faries, Jr. | A61F 7/0085 128/849 |
| 2007/0265586 A1* | 11/2007 | Joshi | A61M 1/0025 604/313 |
| 2008/0071214 A1* | 3/2008 | Locke | A61N 5/0616 604/111 |
| 2008/0148817 A1* | 6/2008 | Miller | G01M 3/04 73/40 |
| 2008/0234641 A1* | 9/2008 | Locke | A61M 1/0031 604/313 |
| 2009/0227969 A1* | 9/2009 | Jaeb | A61F 13/00063 604/313 |
| 2009/0238811 A1* | 9/2009 | McDaniel | C09D 5/00 424/94.2 |
| 2009/0301382 A1* | 12/2009 | Patel | G01N 31/229 116/201 |
| 2010/0030167 A1* | 2/2010 | Thirstrup | A61F 13/42 604/318 |
| 2010/0233146 A1* | 9/2010 | McDaniel | C09D 5/14 424/94.2 |
| 2010/0234818 A1* | 9/2010 | Aali | A61F 13/0226 604/290 |
| 2011/0015619 A1* | 1/2011 | Svedman | A61M 1/0088 604/543 |
| 2011/0092958 A1 | 4/2011 | Jacobs | |
| 2011/0130642 A1* | 6/2011 | Jaeb | A61N 1/0468 600/407 |
| 2011/0130712 A1* | 6/2011 | Topaz | A61F 13/00029 604/23 |
| 2011/0245682 A1* | 10/2011 | Robinson | A61M 1/0025 600/473 |
| 2011/0250626 A1* | 10/2011 | Williams | C12Q 1/34 435/18 |
| 2011/0259086 A1* | 10/2011 | Harris | G01N 31/225 73/40.7 |
| 2011/0275159 A1* | 11/2011 | Landgrebe | G01N 31/226 436/1 |
| 2013/0066285 A1* | 3/2013 | Locke | A61M 1/0088 604/318 |
| 2013/0102979 A1* | 4/2013 | Coulthard | A61F 13/00063 604/319 |
| 2014/0088534 A1* | 3/2014 | Kanakkanatt | C09D 11/037 604/361 |
| 2014/0154808 A1* | 6/2014 | Patel | A61L 2/07 436/1 |
| 2014/0163491 A1 | 6/2014 | Schuessler et al. | |
| 2015/0080788 A1 | 3/2015 | Blott et al. | |
| 2017/0224890 A1* | 8/2017 | Locke | A61M 1/009 |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| EP | 2098257 A1 | 9/2009 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 9324820 A1 | 12/1993 |
| WO | 94/020041 A1 | 9/1994 |
| WO | 96/05873 A1 | 2/1996 |
| WO | 97/18007 A1 | 5/1997 |

(56) References Cited

FOREIGN PATENT DOCUMENTS

| WO | 99/13793 A1 | 3/1999 |
|---|---|---|
| WO | 2008143628 A1 | 11/2008 |
| WO | 2011/049562 A1 | 4/2011 |

OTHER PUBLICATIONS

International Search Report and Written Opinion for corresponding PCT/US2012/050314, dated May 14, 2013.
Henriette Kress: "Litmus", The British Pharmaceutical Codex, Dec. 31, 1911, pp. 1-2, XP055051026, Retrieved from the Internet: URL :http://www.henriettesherbal.com/eclectic /bpc1911 /roccella.html [retrieved on Jan. 24, 2013] p. 1-p. 2.
Andrew Mills: "Oxygen indicators and intelligent inks for packaging food", Chemical Society Reviews, vol. 34, No. 12, Jan. 1, 2005, p. 1003, XP055050325, ISSN: 0306-0012, DOI: 10.1039/b503997p the whole document.
Mills A et al.: "Nanocrystalline Sn02-based, UVB-activated, colourimetric oxygen indicator", Sensors and Actuators B: Chemical: International Journal Devoted to Research and Development of Physical and Chemical Transducers, Elsevier S.A. Switzerland, vol. 136, No. 2, Mar. 2, 2009. pp. 344-349, XP025946493, ISSN: 0925-4005, DOI: 10.1016/J.SNB.2008.12.048 [retrieved on Dec. 31, 2008] *introduction*.
Louis C. Argenta, MD and Michael J. Morykwas, PhD; Vacuum-Assisted Closure: A New Method for Wound Control and Treatment: Clinical Experience; Annals of Plastic Surgery.
Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 198, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & dated Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al: "Closed Wound Suction Drainage", The Journal of Foot Surgery, vol. 24, No. 1, 1985, pp. 76-81.
Arnljots, Björn et al: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax,"Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, (56) References Cited

OTHER PUBLICATIONS edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C. ® Therapy Clinical Guidelines: A Reference Source for Clinicians; Jul. 2007.

Extended Search Report for Corresponding Application No. 182060913, dated Feb. 28, 2019.

\* cited by examiner

REDUCED-PRESSURE SYSTEMS AND METHODS EMPLOYING A LEAK-DETECTION MEMBER

RELATED APPLICATIONS

This application is a continuation of U.S. patent application Ser. No. 13/571,860, filed Aug. 10, 2012, which claims the benefit, under 35 USC § 119(e), of the filing of U.S. Provisional Patent Application Ser. No. 61/534,566, entitled "Reduced-Pressure Systems and Methods Employing a Leak-Detection Member," by Locke et al., filed Sep. 14, 2011. These applications are incorporated herein by reference for all purposes.

BACKGROUND

The present disclosure relates generally to medical treatment systems and, more particularly, but not by way of limitation, to reduced-pressure systems and methods employing a leak-detection member.

Clinical studies and practice have shown that providing a reduced pressure in proximity to a tissue site augments and accelerates the growth of new tissue at the tissue site. The applications of this phenomenon are numerous, but application of reduced pressure has been particularly successful in treating wounds. This treatment (frequently referred to in the medical community as "negative pressure wound therapy," "reduced pressure therapy," or "vacuum therapy") provides a number of benefits, which may include faster healing and increased formulation of granulation tissue. Typically, reduced pressure is applied to tissue through a porous pad or other manifold device. The porous pad contains cells, pores, or pathways that are capable of distributing reduced pressure to the tissue and channeling fluids that are drawn from the tissue. The porous pad is typically covered by a drape that forms a seal.

SUMMARY

According to an illustrative embodiment, a system for treating a tissue site on a patient with reduced pressure includes a distribution manifold for disposing proximate to the tissue site and a sealing member for disposing over the distribution manifold and at least a portion of intact epidermis of the patient. The sealing member has at least a portion that is substantially transparent. The system further includes a reduced-pressure source associated with the distribution manifold for providing reduced pressure to the distribution manifold and a leak-detection member sized and configured to substantially surround the distribution manifold. The leak-detection member includes a detection material that develops a color contrast when a portion of the detection material is exposed to air and a portion of the detection material is not exposed to air.

According to another illustrative embodiment, a method for providing reduced-pressure treatment to a tissue site on a patient, the method includes disposing a distribution manifold proximate to the tissue site and disposing a leak-detection member around the distribution manifold. The leak-detection member comprises a detection material that develops a color contrast when a portion of the detection material is exposed to air and a portion is not exposed to air. The method further includes covering the distribution manifold and leak-detection member with a sealing member. The sealing member has at least a portion that is substantially transparent. The method also includes providing reduced pressure to the distribution manifold, identifying a first color contrast on the leak-detection member indicative of a first leak, and sealing the first leak.

According to another illustrative embodiment, a system for treating a tissue site on a patient with reduced pressure includes a distribution manifold for disposing proximate to the tissue site and a sealing member for disposing over the distribution manifold and at least a portion of intact epidermis of the patient. The sealing member has at least a portion that is substantially transparent. The system further includes a reduced-pressure source associated with the distribution manifold for providing reduced pressure to the distribution manifold and a leak-detection member sized and configured to substantially surround the distribution manifold. The leak-detection member comprises a detection material that develops a color contrast when a portion of the detection material is exposed to a challenge gas and a portion is not exposed to the challenge gas. The system also includes a challenge gas distributor for spraying challenge gas onto the sealing member.

According to another illustrative embodiment, a method for providing reduced-pressure treatment to a tissue site on a patient includes disposing a distribution manifold proximate to the tissue site and disposing a leak-detection member around the distribution manifold. The leak-detection comprises a detection material that develops a color contrast when a portion is exposed to a challenge gas and a portion is not exposed to the challenge gas. The method further includes covering the distribution manifold and leak-detection member with a sealing member. The sealing member has at least a portion that is substantially transparent. The method also includes providing reduced pressure to the distribution manifold, spraying the challenge gas onto the sealing member, identifying a first color contrast on the leak-detection member indicative of a first leak, and sealing the first leak.

According to another illustrative embodiment, a system for treating a tissue site on a patient with reduced pressure includes a distribution manifold for disposing proximate to the tissue site and a sealing member for disposing over the distribution manifold and at least a portion of intact epidermis of the patient. The sealing member has at least a portion that is substantially transparent. The system further includes a reduced-pressure source associated with the distribution manifold for providing reduced pressure to the distribution manifold and a skin-preparation fluid comprising a detection material that develops a color contrast when a portion of the detection material is exposed to air and a portion is not exposed to air.

According to another illustrative embodiment, a system for treating a tissue site on a patient with reduced pressure includes a distribution manifold for disposing proximate to the tissue site and a sealing member for disposing over the distribution manifold and at least a portion of intact epidermis of the patient. The tissue-facing side of the sealing member is covered at least partially with a first agent. The sealing member has at least a portion that is substantially transparent. The system further includes a reduced-pressure source associated with the distribution manifold for providing reduced pressure to the distribution manifold and a skin-preparation fluid comprising a second agent. When the first agent of the sealing member and the second agent of the skin-preparation fluid combine, the two agents form a contact color that is indicative of contact between the first agent and second agent.

According to another illustrative embodiment, a method for treating a tissue site on a patient with reduced pressure includes the steps of disposing a distribution manifold adjacent to the tissue site and covering the distribution manifold with a sealing member. The sealing member has a first agent. The sealing member has at least a portion that is substantially transparent. The method further includes disposing a skin-preparation fluid onto epidermis proximate to and around the tissue site. The skin-preparation fluid has a second agent. The first agent of the sealing member and the second agent of the skin-preparation fluid combine to form a contact color indicative of contact between the first agent and second agent. The method also includes identifying any locations on a peripheral portion of the sealing member lacking the contact color and applying a force to the location on the peripheral portion of the sealing member that was lacking the contact color.

According to another illustrative embodiment, a method of manufacturing a system for treating a tissue site on a patient with reduced pressure includes the steps of forming a distribution manifold for disposing proximate to the tissue site and forming a sealing member for disposing over the distribution manifold and at least a portion of intact epidermis of the patient. The sealing member has at least a portion that is substantially transparent. The method further includes providing a reduced-pressure source for fluidly coupling to the distribution manifold and forming a leak-detection member sized and configured to substantially surround the distribution manifold. The leak-detection member comprises a detection material that develops a color contrast when a portion of the detection material is exposed to air and a portion is not exposed to air.

According to another illustrative embodiment, a system for treating a tissue site on a patient with reduced pressure includes a distribution manifold for disposing proximate to the tissue site and a sealing member for disposing over the distribution manifold and at least a portion of intact epidermis of the patient. The sealing member has at least a portion that is substantially transparent. The sealing member comprises a film that is at least partially covered on a tissue-facing side with a hydrophilic adhesive. The system further includes a reduced-pressure source associated with the distribution manifold for providing reduced pressure to the distribution manifold. Under reduced pressure, fluid exudate from the tissue site is brought into contact with the hydrophilic adhesive in locations where reduced pressure is acting and is not brought into contact with the hydrophilic adhesive in locations where reduced pressure is not acting. A color contrast is thereby created.

According to another illustrative embodiment, a method for treating a tissue site on a patient with reduced pressure includes the steps of disposing a distribution manifold proximate to the tissue site and covering the distribution manifold and a portion of intact epidermis of the patient with a sealing member. The sealing member has at least a portion that is substantially transparent. The sealing member comprises a film that is at least partially covered on a tissue-facing side with a hydrophilic adhesive. The method further includes fluidly coupling a reduced-pressure source to the distribution manifold to provide reduced pressure to the distribution manifold whereby the reduced pressure moves exudate into contact with the hydrophilic adhesive in locations where reduced pressure is acting and does not move exudate to locations where reduced pressure is not acting. The method also includes identifying locations where exudate is not brought into contact with the hydrophilic adhesive as potential leak locations and sealing the potential leak locations.

Other features and advantages of the illustrative embodiments will become apparent with reference to the drawings and detailed description that follow.

DETAILED DESCRIPTION OF ILLUSTRATIVE EMBODIMENTS

In the following detailed description of the illustrative, non-limiting embodiments, reference is made to the accompanying drawings that form a part hereof. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments are defined only by the appended claims.

Figure 1:
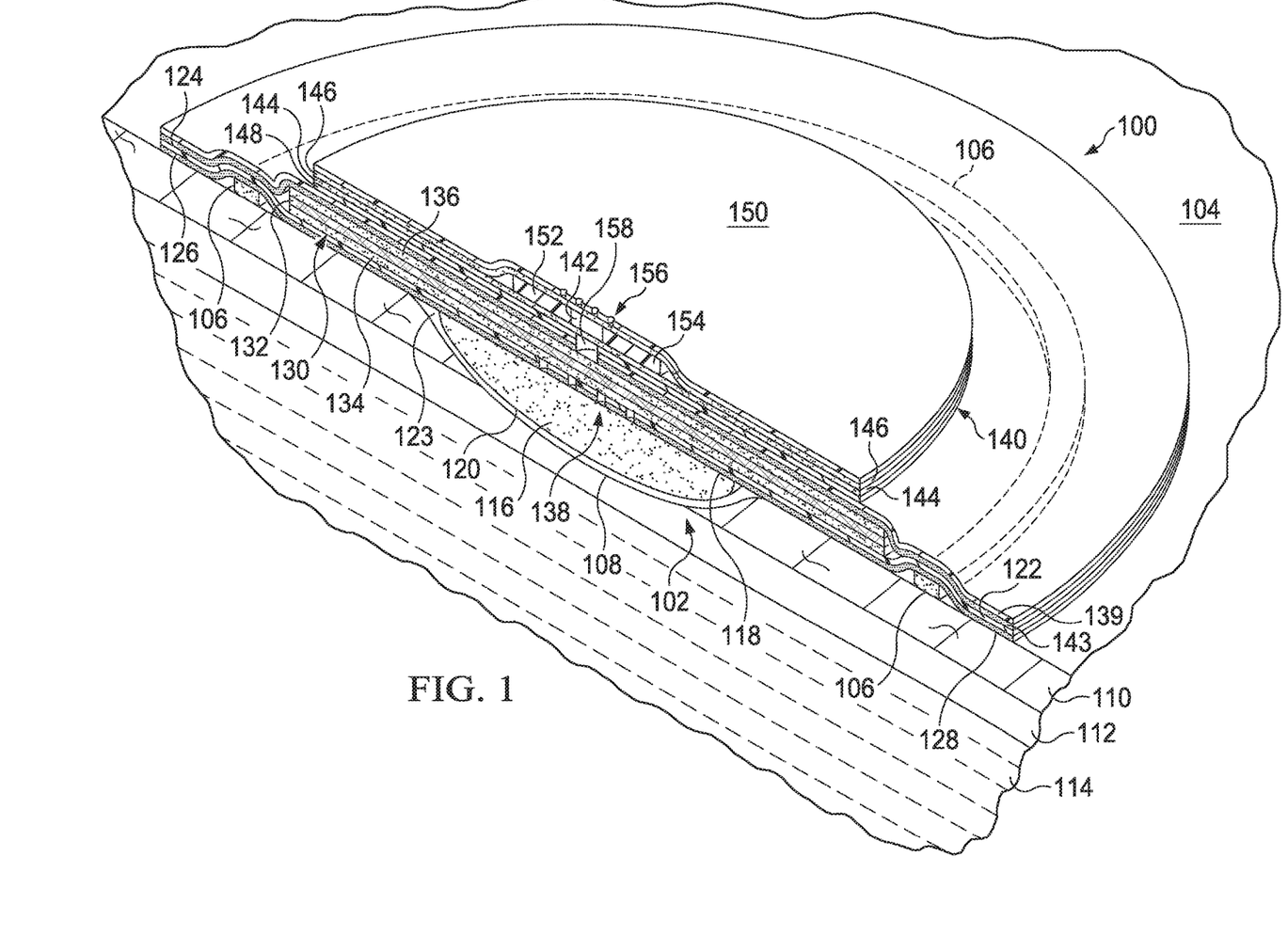
FIG. 1 is a schematic diagram, with a portion shown in cross section and a portion shown in perspective view, of an illustrative embodiment of a system for treating a tissue site on a patient with reduced pressure.

Referring now to the drawings and initially and primarily to FIG. 1, a system 100 for treating a tissue site 102 on a patient 104 with reduced pressure is presented that includes a leak-detection member 106. The tissue site 102 may be, as a non-limiting example, an open wound 108 involving a patient's epidermis 110, dermis 112, and possibly subcutaneous tissue 114. In other examples, the tissue site 102 may be a surface wound on the patient's epidermis 110 or at another tissue site. The tissue site 102 may be the bodily tissue of any human, animal, or other organism, including bone tissue, adipose tissue, muscle tissue, dermal tissue, vascular tissue, connective tissue, cartilage, tendons, ligaments, or any other tissue. Treatment of the tissue site 102 may include the removal of fluids, e.g., exudate or ascites.

The system 100 includes a distribution manifold 116 for disposing proximate to the tissue site 102. The distribution manifold 116 has a first side 118 and a second, tissue-facing side 120. The distribution manifold 116 references a substance or structure that is provided to assist in applying reduced pressure to, delivering fluids to, or removing fluids from the tissue site 102. The distribution manifold 116 typically includes a plurality of flow channels or pathways that distribute fluids provided to and removed from the tissue site 102 around the distribution manifold 116. In one illustrative embodiment, the flow channels or pathways are interconnected to improve distribution of fluids provided or removed from the tissue site 102. The distribution manifold 116 may be a biocompatible material that is capable of being placed in contact with the tissue site 102 and distributing reduced pressure to the tissue site 102. Examples of the distribution manifold 116 may include, without limitation, devices that have structural elements arranged to form flow channels, such as, for example, cellular foam, open-cell foam, porous tissue collections, liquids, gels, and foams that include, or cure to include, flow channels. The distribution manifold 116 may be porous and may be made from foam, gauze, felted mat, or any other material suited to a particular biological application. In one embodiment, the distribution manifold 116 is a porous foam and includes a plurality of interconnected cells or pores that act as flow channels. The porous foam may be a polyurethane, open-cell, reticulated foam such as GranuFoam® material manufactured by Kinetic Concepts, Incorporated of San Antonio, Tex. In some situations, the distribution manifold 116 may also be used to distribute fluids such as medications, antibacterials, growth factors, and various solutions to the tissue site 102. Other layers may be included in or on the distribution manifold 116, such as absorptive materials, wicking materials, hydrophobic materials, and hydrophilic materials.

In one illustrative embodiment, the distribution manifold 116 may be constructed from bioresorbable materials that do not have to be removed from a patient's body following use of the system 100. Suitable bioresorbable materials may include, without limitation, a polymeric blend of polylactic acid (PLA) and polyglycolic acid (PGA). The polymeric blend may also include without limitation polycarbonates, polyfumarates, and capralactones. The distribution manifold 116 may further serve as a scaffold for new cell-growth, or a scaffold material may be used in conjunction with the distribution manifold 116 to promote cell-growth. A scaffold is a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

The system 100 also includes a first or lower sealing member 122 for disposing over the distribution manifold 116 and at least a portion of the intact epidermis 110 of the patient 104. The lower sealing member 122 creates a sealed space 123 that contains the distribution manifold 116. The lower sealing member 122 has a first side 124 and a second, tissue-facing side 126. The lower sealing member 122 has at least a portion that is substantially transparent so that colors and color contrasts on the leak-detection member 106 may be seen through the lower sealing member 122. The lower sealing member 122 is typically a drape, but the lower sealing member 122 may be any material that provides a fluid seal under normal operating conditions. The lower sealing member 122 may, for example, be an impermeable or semi-permeable, elastomeric material. As used herein, elastomeric means having the properties of an elastomer. Elastomeric generally refers to a polymeric material that has rubber-like properties. More specifically, most elastomers have ultimate elongations greater than 100% and a significant amount of resilience. The resilience of a material refers to the material's ability to recover from an elastic deformation. Examples of elastomers may include, but are not limited to, natural rubbers, polyisoprene, styrene butadiene rubber, chloroprene rubber, polybutadiene, nitrile rubber, butyl rubber, ethylene propylene rubber, ethylene propylene diene monomer, chlorosulfonated polyethylene, polysulfide rubber, polyurethane (PU), EVA film, co-polyester, and silicones. Additional, specific examples of sealing member materials include a silicone drape, a 3M Tegaderm® drape, or a polyurethane (PU) drape such as one available from Avery Dennison Corporation of Pasadena, Calif.

A first attachment device 128 may be used to hold the lower sealing member 122 against the patient's epidermis 110 or another layer, such as a gasket or additional sealing member. The first attachment device 128 may take numerous forms. For example, the first attachment device 128 may be a medically acceptable, pressure-sensitive adhesive that extends about a periphery, a portion, or the entire lower sealing member 122. As additional examples, the attachment device 128 may be a double-sided drape tape, paste, hydrocolloid, hydro gel or other sealing devices or elements. The first attachment device 128 may also be a sealing ring or other device. The first attachment device 128 is disposed on the second, tissue-facing side 126 of the lower sealing member 122. Before use, the first attachment device 128 may be covered by a release liner (not shown).

A liquid receptor 130 is fluidly coupled to the tissue site 102 for receiving and, at least partially, retaining liquids. In the illustrative embodiment of FIG. 1, the liquid receptor 130 is formed by an absorbent layer 132 and may also include a first wicking layer 134 and a second wicking layer 136. The wicking layers 134, 136 sandwich the absorbent layer 132. The wicking layers 134, 136 are fluid permeable and attract liquids. The absorbent layer 132 may, as a non-limiting example, be a layer of super absorbent fibers. The absorbent layer 132 may be fluidly coupled through apertures 138 to the lower sealing member 122, the first attachment device 128, and consequently to the tissue site 102.

An upper sealing member 139 may be coupled with a second attachment device 143 to a portion of the lower sealing member 122. Thus, the lower sealing member 122 and upper sealing member 139 may sandwich the absorbent layer 132 and the wicking layers 134, 136. The upper sealing member 139 may also be substantially transparent, at least at portions, so that contrasts on the leak-detection member 106 may be seen through the upper sealing member 139.

The system 100 also includes a reduced-pressure source 140 associated with the distribution manifold 116 for providing reduced pressure to the sealed space 123 and, in particular, to the distribution manifold 116. While the reduced-pressure source 140 may be any device for supplying a reduced pressure, such as a vacuum pump, wall suction, micro-pump, or other source, in the illustrative embodiment of FIG. 1, the reduced-pressure source 140 is a micro-pump 142 that is adjacent to the liquid receptor 130. While the amount and nature of reduced pressure applied to a tissue site will typically vary according to the application, the reduced pressure will typically be between −5 mm Hg and −500 mm Hg and more typically between −75 mm Hg and −300 mm Hg.

The micro-pump 142 may be a piezoelectric pump that may be sandwiched between two foam cushion layers 144, 146. The two foam cushion layers 144, 146 may themselves be sandwiched between a lower ply 148 and an upper ply 150. The lower ply 148 and upper ply 150 may be bonded at their peripheries. A first power unit 152 and a control unit 154 may be positioned between the lower ply 148 and the upper ply 150 and may be coupled to the micro-pump 142 for powering and controlling the micro-pump 142. The micro-pump 142 may exhaust air through a plurality of apertures 156 in the upper ply 150. A central aperture 158 may fluidly couple a lower pressure side or suction side of the micro-pump 142 to the second wicking layer 136. Reduced pressure may thereby be delivered through the second wicking layer 136, absorbent layer 132, and apertures 138 to the sealed space 123 and ultimately to the tissue site 102.

The system 100 also includes the leak-detection member 106. The leak-detection member 106 allows a user to identify leaks of air or certain gases from an exterior through a location where a substantially gas tight seal has not been formed between the lower sealing member 122 and the patient's epidermis 110. The leak-detection member 106 may be sized and configured to substantially surround the distribution manifold 116. The leak-detection member 106 surrounds at least where reduced pressure enters the sealed space 123. The leak-detection member 106 may comprise a detection material that is reactive to air, including carbon dioxide and oxygen to develop a color contrast when a portion is exposed to air and a portion is not exposed to air.

The leak-detection member 106 may be a curved member that is disposed around (substantially 360 degrees about) the tissue site 102 being treated or around the distribution manifold 116. If air leaks between the epidermis 110 and the lower sealing member 122, a color contrast will develop on a portion of a leak path where the leak path encounters the leak-detection member 106. The user may then visually identify the leak location since the leak location coincides with the color contrast. The user may then seal the leak. The leak may be sealed by rubbing on the lower sealing member 122 to improve the seal or by adding additional sealing members along an edge or periphery of the lower sealing member 122 where the air first enters.

The leak-detection member 106 is formed from the detection material. The detection material may be an agent alone or combined with an adhesive. The agent may respond visually to the amount of oxygen ($O_2$), carbon dioxide ($CO_2$), or other gas present. Thus, for example, if more oxygen or more carbon dioxide is present at one location on the leak-detection member 106 than at another location, as is the case with a leak in which air enters, a visual indication will be established in the form of a color contrast. The leak-detection member 106 may allow leaks with low flow, e.g., as low as or less than 0.2 ml/hour, to be identified.

Figure 2:
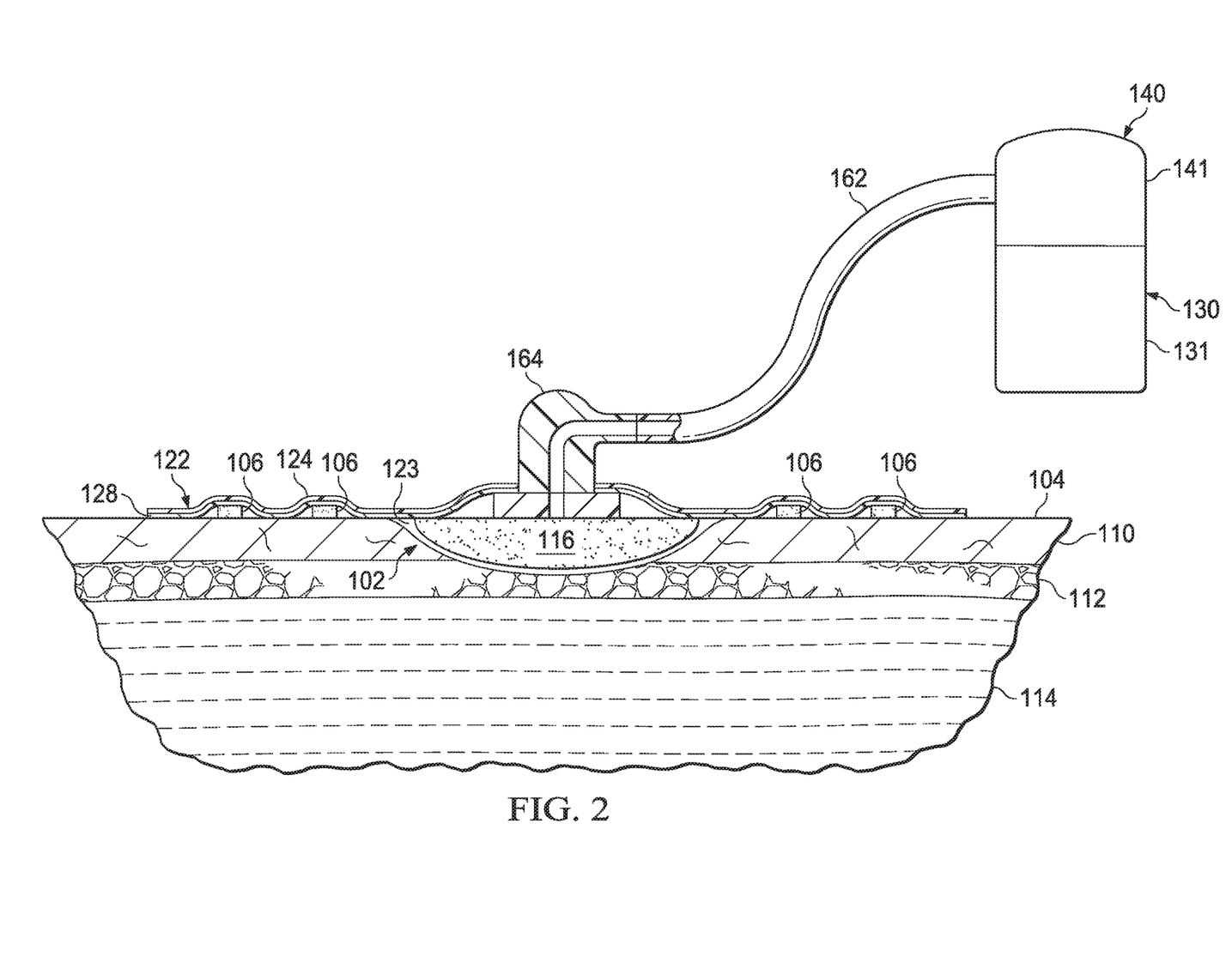
FIG. 2 is a schematic, cross-section of an illustrative embodiment of a system for treating a tissue site on a patient with reduced pressure.

The leak-detection member 106 may substantially surround the tissue site 102. Thus, when a leak occurs in any direction, the leak may be identified. The leak-detection member 106 may be a single ring as shown in FIG. 1 or a plurality of rings or members or other shapes as shown in FIGS. 2, 3, and 4. The leak-detection member 106 may also be formed from curved segments that are spaced. The curved segments preferably cover 360 degrees around the tissue site 102 so that a leak path in any direction may be identified. In another illustrative embodiment, the leak-detection member 106 may be a region on the tissue-facing side 126 of the lower sealing member 122 or may be concomitant with the tissue-facing side 126 of the lower sealing member 122 altogether.

In one illustrative embodiment, the detection material may be a material that changes color or reacts as the pH changes. Under normal atmospheric conditions, e.g., with normal levels of carbon dioxide, the pH of water will be about 5.7. (Carbon dioxide requires the presence of water to form a weak acid resulting in a pH drop; similarly, ammonia requires moisture to form a weak base). If carbon dioxide is used as a challenge gas, which will be explained further below, the pH will be lower (3-4). In any event, the pH will increase when ammonia gas is detected and will decrease when carbon dioxide is detected. The change in pH results in a change in the color. Thus, as the pH changes in a location but not in other locations, the color changes and creates a color contrast. Detection materials that respond as such to pH changes include the following: litmus, bromocresol purple, bromocresol blue, azolitmin, methyl red, bromocresol green. The detection material may also be a REDOX-based dye that is sensitive to oxygen. Illustrative examples of REDOX-based dyes that are sensitive to oxygen include the following: methylene Blue (available from Sigma), N-phenylanthranilic acid (available from Acros Organics), or Neutral Red (available from Fisher Scientific).

As another illustrative detection material, titanium dioxide and glycerol may be used. A mixture of titanium dioxide, methylene blue and glycerol becomes a colorimetric indicator for oxygen after activation by UV. The titanium dioxide oxidizes the glycerol (a sacrificial electron donor), reduces the REDOX dye methylene blue to a colorless form until, on exposure to oxygen, the reduced methylene blue is oxidized back to its blue color.

In one illustrative embodiment, the detection material may be a ultraviolet (UV) light sensitive ink. When exposed to UV, the ink becomes colorless and sensitive to oxygen such that a blue color forms under the influence of oxygen. Thus, the leak path will show a blue on a portion that is in contrast to the color on the non-leaking portions. The non-leaking portions starve the ink of oxygen and become colorless. Thus, the leak-detection member 106 may include such an ink and a detection tool, e.g., a UV light tool, may be activated to give off UV light and help identify any leak paths.

In another illustrative example, the detection material is a phosphorescence material that becomes more fluorescent or less fluorescent when exposed to air. Thus, a user may cause portions of the leak-detection member 106 to become fluorescent by exposing the leak-detection member 106 to a detection tool, e.g., UV light or Infrared light tool. If a leak exists, the gas in the air will cause the detection material to be more or less fluorescent depending on the specific material used.

In one illustrative embodiment, the detection material includes a fluorescent agent that will fluoresce in response to UV light or IR and that is disposed on the tissue-facing side 126 of the lower sealing member 122. The detection material will fluoresce until the fluorescent agent contacts moisture and salt that are common on the epidermis 110. Upon coming into contact with the moisture and salt, the detection material will discontinue to fluoresce or not fluoresce with the same strength (fluorescence quenching). In areas where no such contact is made between the detection material and the epidermis 110, the detection material will continue to fluoresce. Thus, the user may observe a color contrast in locations where a leak is probably located, i.e., where the lower sealing member 122 is not contacting the epidermis 110.

In another illustrative embodiment, the leak-detection member 106 includes a detection material that fluoresces under UV or IR even when in contact with the epidermis 110. The detection material, however, experiences fluorescent quenching when exposed to oxygen. Thus, the leak path will fluoresce less and will have a color contrast.

In another illustrative embodiment, the detection material is a material that responds to a challenge gas. A challenge gas is a gas presented on an outside of the sealing member. If a leak exists, the challenge gas is pulled into the leak path and reacts with the detection material. For example, after applying the system 100, the user may spray the challenge gas using a challenge gas distributor. The challenge gas is typically heaver than air. The challenge gas is sprayed onto the sealing member, and if a leak exists, the challenge gas will enter the leak path and cause the detection material to take on a color contrast.

Continuing to refer primarily to FIG. 1, in operation, the user disposes the distribution manifold 116 proximate to the tissue site 102 that is to be treated. The user then disposes the leak-detection member 106 around the tissue site 102 or distribution manifold 116. The user disposes the lower sealing member 122 over the distribution manifold 116 and the leak-detection member 106. The leak-detection member 106 may already be attached to the second, tissue-facing side 126 of the lower sealing member 122 and may be applied as an aspect of disposing the lower sealing member 122 or may be disposed separately on the patient's epidermis 110. In one illustrative embodiment, disposing the leak-detection member 106 may involve disposing a curved member formed from the detection material onto the epidermis 110 of the patient 104 outboard of the tissue site 102. In another illustrative embodiment, disposing the leak-detection member 106 around the distribution manifold 116 may involve applying a liquid that comprises the detection material onto the intact epidermis 110 of the patient 104 outboard of the tissue site 102.

Reduced pressure is then provided to the distribution manifold 116, e.g., by activating the micro-pump 142. After the system 100 operates for a period of time, if any leaks exist, air will be pulled into the leak path and the leak-detection member 106 will develop a color contrast as previously noted. The color contrast coincides with a portion of the leak path, and the user may use the visual cue to locate the leak. The user may then seal the leak by applying force or rubbing the leak path or by applying additional sealing members at an edge of the lower sealing member 122 proximate to the identified leak path.

Referring now primarily to FIG. 2, another illustrative embodiment of the system 100 for providing reduced pressure to the tissue site 102 on the patient 104 is presented. The system is analogous in many respects to the system 100 of FIG. 1. In this embodiment, however, the reduced-pressure source 140 is an external reduced-pressure source 141 and the liquid receptor 130 is a canister or other external fluid reservoir 131.

The external reduced-pressure source 141 is fluidly coupled by a reduced-pressure delivery conduit 162 to a reduced-pressure interface 164. In one illustrative embodiment, the reduced-pressure interface 164 is a T.R.A.C.® Pad or Sensa T.R.A.C.® Pad available from KCI of San Antonio, Tex. The reduced-pressure interface 164 allows the reduced pressure to be delivered to the distribution manifold 116.

In this illustrative embodiment, only the lower or first sealing member 122 is used and the leak-detection member 106 includes two concentric members. The concentric members forming the leak-detection member 106 are shown best in FIGS. 3A-3B. Because in this illustrative embodiment the lower sealing member 122 is transparent, the portions beneath (on the tissue-facing side) of the lower sealing member 122 are shown without hidden lines. Other structural aspects of the system 100 of FIG. 2 are analogous to FIG. 1 and are not further described.

Figure 3A:
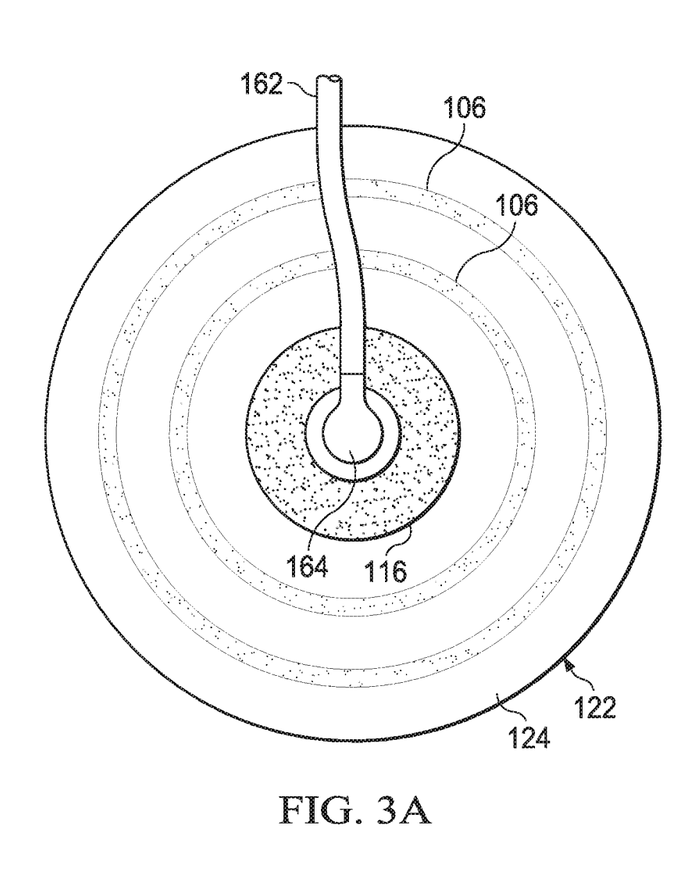
FIG. 3A is a schematic, top plan view of a portion of the system of FIG. 2.

Referring now primarily to FIG. 3A, a portion of the system of FIG. 2 is presented in plan view. In FIG. 3A, either the system 100 has not been activated or has been activated but no leak has been detected. No leak is detected as shown by the absence of any color contrast on the leak-detection member 106. On the other hand, in FIG. 3B, a leak path 166 is shown by color contrasts 168 on the leak-detection member 106. While generally not visible (other than the color contrasts 168), the leak path 166 is shown with broken lines beginning at an edge or periphery 170 and extending to the distribution manifold 116 from where the leak flows into the reduced-pressure interface 164.

Figure 3B:
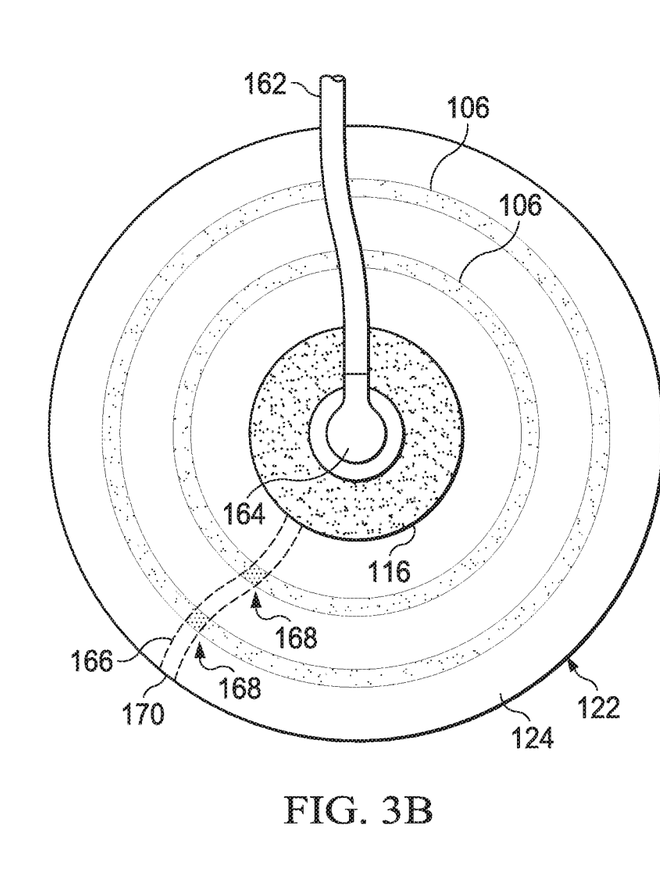
FIG. 3B is the portion of a reduced-pressure system shown in FIG. 3A with a leak shown.
Figure 4:
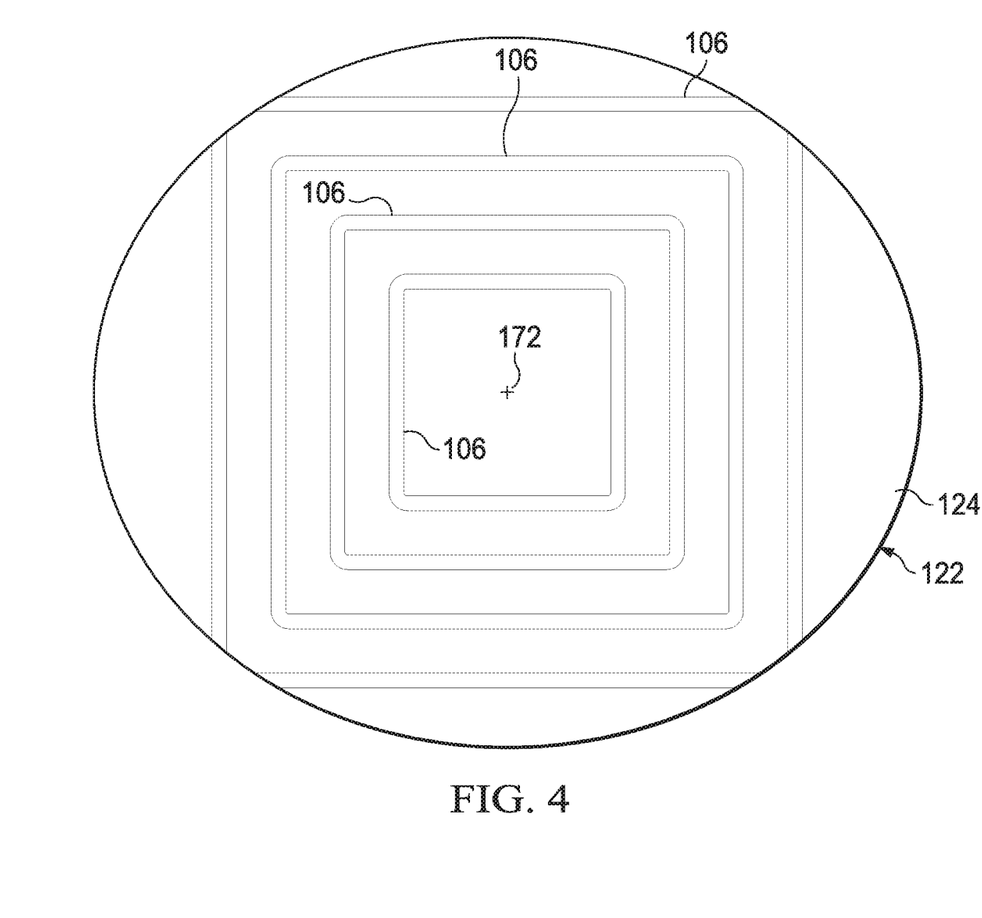
FIG. 4 is a schematic, top plan view of an illustrative embodiment of a sealing member and a leak-detection member.

Application of the system 100 of FIGS. 2-3B is analogous to that presented for the system 100 of FIG. 1. It should be noted that in the various embodiments, the leak-detection member 106 may take many forms. The leak-detection member may be a single ring, a single member of any shape, a plurality of concentric members such as concentric circles shown in FIGS. 3A-3B or concentric squares shown in FIG. 4, a plurality of spaced curved segments, or any other arrangement that will allow leak paths in any direction to be detected.

Referring now primarily to FIG. 4, an illustrative embodiment of the lower sealing member 122 and leak-detection member 106 are presented. In this embodiment, the reduced-pressure source 140 has not yet been applied. Visual indicia 172 may be included on the lower sealing member 122 to aid the user in centering the lower sealing member 122 on the tissue site.

Figure 5:
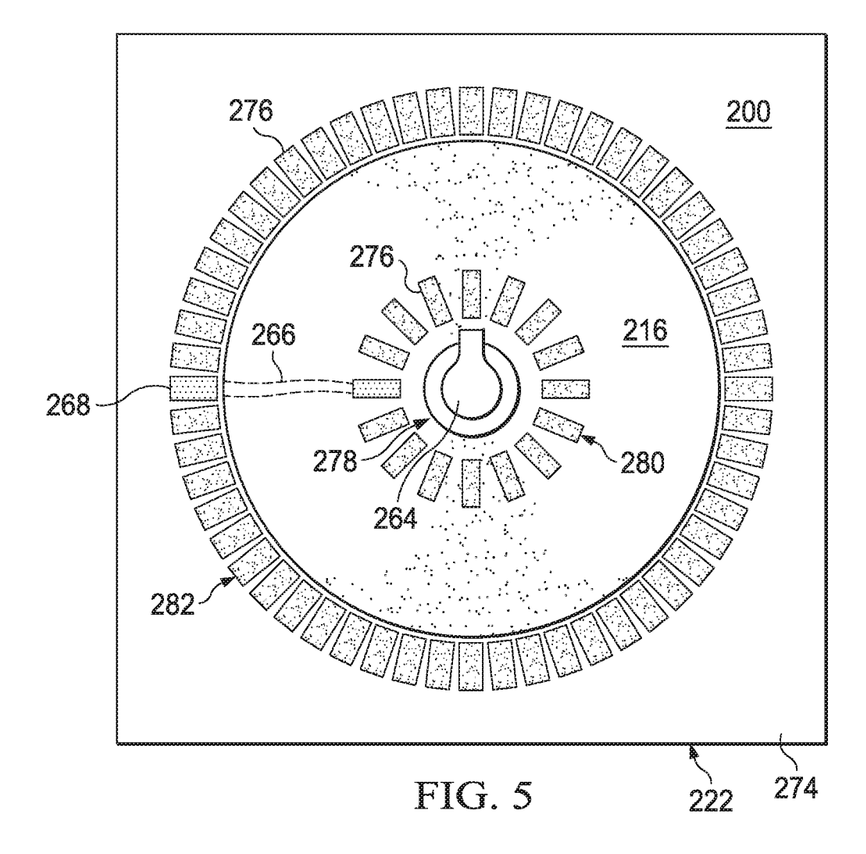
FIG. 5 is a schematic, top plan view of an illustrative embodiment of a portion of a system for treating a tissue site on a patient with reduced pressure.

Referring now primarily to FIG. 5, a portion of an illustrative embodiment of a system 200 for treating a tissue site, e.g., tissue site 102 in FIG. 1, on a patient with reduced pressure is presented. The system 200 is analogous in many respects to the system of FIG. 1, and analogous parts have been indicated by indexing the reference numerals by 100. The system 200 includes a distribution manifold 216 for disposing proximate to the tissue site. The system 200 also includes a sealing member 222 for disposing over the distribution manifold 216 and at least a portion of intact epidermis of the patient. The sealing member 222 has at least a portion that is substantially transparent to allow viewing of color contrasts. The sealing member 222 includes a film that is at least partially covered on a tissue-facing side with a hydrophilic adhesive 276. The hydrophilic adhesive 276 is preferably in a pattern that surrounds an entry point 278. The entry point 278 is where reduced pressure enters a sealed space formed by the sealing member 222. The entry point 278 may be, for example, where a reduced-pressure interface 264 is fluidly coupled to the sealed space. The sealed space is analogous to the sealed space 123 in FIGS. 1 and 2. In the illustrative embodiment of FIG. 5, the pattern of the hydrophilic adhesive 276 includes a first ring 280 relatively near the entry point 278 and inboard of the peripheral edge of the distribution manifold 216 and a second ring 282 outboard of the distribution manifold 216.

The system 200 includes a reduced-pressure source that is not explicitly shown but is analogous to the external reduced-pressure source 141 of FIG. 2. The reduced pressure source 141 is associated with the distribution manifold 216 for providing reduced pressure to the distribution manifold 216. Under the influence of reduced pressure, fluid exudate from the tissue site is brought into contact with the hydrophilic adhesive 276 at locations where reduced pressure is acting and is not brought into contact with the hydrophilic adhesive 276 at locations where reduced pressure is not acting. Thus, where a leak path 266 appears, the reduced pressure will be dissipated and the exudate will not be brought into contact with the hydrophilic adhesive 276. Because the exudate has a color or tint, the locations on the patterned hydrophilic adhesive 276 where the leak exists will present a color contrast 268. As with the previous embodiments, the color contrast 268 shows the location of the leak path and the leak may be sealed.

Referring again to FIGS. 1-4, according to an illustrative non-limiting embodiment, the leak-detection member 106 may be a skin-preparation fluid or included as an aspect of a skin-preparation fluid. The skin-preparation fluid includes a detection material that develops a color contrast when a portion is exposed to air and a portion is not exposed to air. The skin-preparation fluid is applied at least around the tissue site. The tissue site is surrounded by the skin-preparation fluid. As a non-limiting example of the skin-preparation fluid, in addition to skin preparation liquids, a REDOX color dye or other dye may be included. The lower sealing member 122 is then applied as previously described. If a leak exists, the air contacting the detection material in the skin-preparation fluid will create a color contrast in the skin-preparation fluid and thereby indicate the location of the leak. In another illustrative embodiment, the skin-preparation fluid includes methylene blue that is applied. After applying other aspects of the system 100, the reduced pressure is applied and the portions of the skin-preparation fluid under the lower sealing member 122 with a substantially air tight seal become starved for oxygen and change colors to become clear. Any portions with a leak will, because of the air flow, remain blue and thereby indicate the leak location.

According to another illustrative embodiment, the system 100 for treating the tissue site 102 on the patient 104 with reduced pressure includes the distribution manifold 116 for disposing proximate to the tissue site 102 and the lower sealing member 122 for disposing over the distribution manifold 116 and at least a portion of the intact epidermis 110 of the patient 104. The tissue-facing side 126 of the lower sealing member 122 is covered at least partially with a first agent. The lower sealing member 122 has at least a portion that is substantially transparent to allow viewing of color contrasts. The system 100 also includes the reduced-pressure source 140 associated with the distribution manifold 116 for providing reduced pressure to the distribution manifold 116 and a skin-preparation fluid.

The skin-preparation fluid includes a second agent. When the first agent of the sealing member and the second agent of the skin-preparation fluid combine, they form a contact color indicative of contact between the first agent and second agent. In places where they do not contact, the color does not change. Thus, in use, the user will be able to see a color contrast at places where the lower sealing member 122 and the skin-preparation fluid on the patient's epidermis 110 are not touching. Such locations are probable leak locations and may be sealed by applying force, e.g., rubbing the probable leak location, or applying additional sealing members at an edge near the probable leak location.

Although the present invention and its advantages have been disclosed in the context of certain illustrative embodiments, it should be understood that various changes, substitutions, permutations, and alterations can be made without departing from the scope of the invention as defined by the appended claims. It will be appreciated that any feature that is described in connection to any one embodiment may also be applicable to any other embodiment.

It will be understood that the benefits and advantages described above may relate to one embodiment or may relate to several embodiments. It will further be understood that reference to "an" item refers to one or more of those items.

The steps of the methods described herein may be carried out in any suitable order, or simultaneously where appropriate.

Where appropriate, aspects of any of the embodiments described above may be combined with aspects of any of the other embodiments described to form further examples having comparable or different properties and addressing the same or different problems.

It will be understood that the above description of preferred embodiments is given by way of example only and that various modifications may be made by those skilled in the art. The above specification, examples and data provide a complete description of the structure and use of exemplary embodiments of the invention. Although various embodiments of the invention have been described above with a certain degree of particularity, or with reference to one or more individual embodiments, those skilled in the art could make numerous alterations to the disclosed embodiments without departing from the scope of the claims.

We claim:

1. A system for treating a tissue site, the system comprising:
    a manifold for disposing proximate to the tissue site;
    a sealing member for disposing over the manifold and at least a portion of intact epidermis, the sealing member configured to have an entry point;
    a first ring of hydrophilic adhesive and a second ring of hydrophilic adhesive disposed between the sealing member and at least one of the manifold and the portion of intact epidermis, the first ring of hydrophilic adhesive comprising a first plurality of rectangular deposits disposed circumferentially around the entry point and the second ring of hydrophilic adhesive comprising a second plurality of rectangular deposits disposed circumferentially around the first ring of hydrophilic adhesive, the first ring of hydrophilic adhesive and the second ring of hydrophilic adhesive configured to develop a color contrast in response to a leak, the color contrast indicating a location of the leak; and
    a reduced-pressure source configured to be fluidly coupled to the manifold through the entry point.

2. The system of claim 1, wherein the first ring of hydrophilic adhesive is coupled to the sealing member.

3. The system of claim 1, wherein the second ring of hydrophilic adhesive is concentric with the first ring of hydrophilic adhesive.

4. The system of claim 1, wherein the first ring of hydrophilic adhesive, the second ring of hydrophilic adhesive, and the entry point are concentric.

5. The system of claim 1, wherein each rectangular deposit of the first plurality of rectangular deposits has a short edge and a long edge, the short edge proximate to the entry point.

6. The system of claim 5, wherein the short edge of each rectangular deposit comprises interior corners, each interior corner adjacent to an interior corner of an adjacent rectangular deposit.

7. The system of claim 1, wherein each rectangular deposit of the first plurality of rectangular deposits has a short edge proximate to the entry point, and each rectangular deposit of the second plurality of rectangular deposits has a short edge proximate to the first ring of hydrophilic adhesive.

8. The system of claim 7, wherein the short edge of each rectangular deposit comprises interior corners, each interior corner adjacent to an interior corner of an adjacent rectangular deposit.

9. A drape for disposing over a distribution manifold and at least a portion of intact epidermis to form a sealed space, the drape comprising:
    a film, the film being substantially transparent and configured to have an entry point;

a first annulus of hydrophilic adhesive coupled to the film and configured to develop a color contrast in response to a leak, the first annulus of hydrophilic adhesive comprising a first plurality of rectangular deposits of hydrophilic adhesive disposed circumferentially around the entry point; and a second annulus of hydrophilic adhesive coupled to the film and configured to develop a color contrast in response to a leak, the second annulus of hydrophilic adhesive comprising a second plurality of rectangular deposits disposed circumferentially around the first annulus of hydrophilic adhesive;

wherein the color contrast indicates a location of the leak.

10. The drape of claim 9, wherein the second annulus of hydrophilic adhesive is concentric with the first annulus of hydrophilic adhesive.

11. The drape of claim 9, wherein the first annulus of hydrophilic adhesive, the second annulus of hydrophilic adhesive, and the entry point are concentric.

12. The drape of claim 9, wherein each rectangular deposit of the first plurality of rectangular deposits has a short edge, a long edge, the short edge proximate to the entry point.

13. The drape of claim 12, wherein the short edge of each rectangular deposit comprises interior corners, each interior corner adjacent to an interior corner of an adjacent rectangular deposit.

14. The drape of claim 9, wherein each rectangular deposit of the second plurality of rectangular deposits has a short edge proximate to the first annulus of hydrophilic adhesive.

15. The drape of claim 14, wherein the short edge of each rectangular deposit comprises interior corners, each interior corner adjacent to an interior corner of an adjacent rectangular deposit.

16. A method of manufacturing a sealing member for treating a tissue site, the method comprising:

providing a film, the film being substantially transparent;

forming a first ring of hydrophilic adhesive in a first pattern, the first pattern comprising a plurality of rectangular deposits of hydrophilic adhesive disposed circumferentially around an entry point, each rectangular deposit having a short edge proximate to the entry point;

coupling the first ring of hydrophilic adhesive to the sealing member; and coupling a second ring of hydrophilic adhesive to the sealing member formed in a second pattern, the second pattern comprising a plurality of rectangular deposits of hydrophilic adhesive disposed circumferentially around the first ring of hydrophilic adhesive;

wherein the first ring of hydrophilic adhesive and the second ring of hydrophilic adhesive are configured to develop a color contrast in response to a leak.

17. The method of claim 16, wherein the method further comprises disposing the second ring of hydrophilic adhesive concentric with the first ring of hydrophilic adhesive.

18. The method of claim 16, wherein the short edge of each rectangular deposit comprises interior corners, each interior corner adjacent to an interior corner of an adjacent rectangular deposit.

19. The method of claim 16, wherein the method further comprises disposing the second ring of hydrophilic adhesive in a second pattern, the second pattern comprising a plurality of rectangular deposits of hydrophilic adhesive disposed circumferentially around the first ring of hydrophilic adhesive, each rectangular deposit of the second pattern having has a short edge proximate to the first ring of hydrophilic adhesive.

20. The method of claim 19, wherein the short edge of each rectangular deposit comprises interior corners, each interior corner adjacent to an interior corner of an adjacent rectangular deposit.

21. The system of claim 1, wherein the first ring is configured to be disposed inboard of a peripheral edge of the manifold.

22. The system of claim 1, further comprising:

a liquid receptor configured to be disposed over the sealing member and fluidly coupled to the tissue site; and an upper sealing member configured to be disposed over the liquid receptor and coupled to a portion of the sealing member.

23. The system of claim 22, wherein the liquid receptor comprises an absorbent layer, a first wicking layer, and a second wicking layer, the absorbent layer configured to be positioned between the first wicking layer and the second wicking layer.

* * * * *

UNITED STATES PATENT AND TRADEMARK OFFICE
CERTIFICATE OF CORRECTION

PATENT NO. : 11,045,593 B2
APPLICATION NO. : 15/449551
DATED : June 29, 2021
INVENTOR(S) : Christopher Brian Locke It is certified that error appears in the above-identified patent and that said Letters Patent is hereby corrected as shown below:

In the Claims

Column 14
Line 18-24, In Claim 19, between "wherein" and "each rectangular" delete "the method further comprises disposing the second ring of hydrophilic adhesive in a second pattern, the second pattern comprising a plurality of rectangular deposits of hydrophilic adhesive disposed circumferentially around the first ring of hydrophilic adhesive,".

Signed and Sealed this
Ninth Day of April, 2024

Katherine Kelly Vidal
*Director of the United States Patent and Trademark Office*